United States Patent [19]

McCaffery, III

[11] Patent Number: 4,629,785

[45] Date of Patent: Dec. 16, 1986

[54] EXTRACTION OF NUTRITIOUS MATERIALS FROM ACIDIC SLUDGE WASTE SOLIDS BY ADSORPTION

[76] Inventor: Thomas F. McCaffery, III, 412 Milford Dr., Broomall, Pa. 19008

[21] Appl. No.: 719,637

[22] Filed: Apr. 4, 1985

Related U.S. Application Data

[63] Continuation of Ser. No. 540,993, Oct. 11, 1983, which is a continuation of Ser. No. 165,084, Jul. 1, 1980, abandoned, which is a continuation-in-part of Ser. No. 887,871, Mar. 20, 1978, abandoned, which is a continuation of Ser. No. 672,349, Mar. 31, 1976, abandoned.

[51] Int. Cl.$^4$ .............................................. C07K 3/18
[52] U.S. Cl. .................................... 530/415; 530/417; 530/859
[58] Field of Search ...................................... 260/112 R

[56] References Cited

U.S. PATENT DOCUMENTS

| | | | |
|---|---|---|---|
| 2,204,703 | 6/1940 | Sanders | 260/112 R X |
| 2,277,718 | 3/1942 | Sanders | 260/112 R X |
| 2,328,361 | 8/1943 | Sanders | 260/112 R |
| 2,389,865 | 11/1945 | Mills et al. | 521/39 |
| 2,446,913 | 8/1948 | Erlich | 260/112 R X |
| 3,002,823 | 10/1961 | Flodin et al. | 260/112 R X |
| 3,520,802 | 7/1970 | Pavia | 260/112 R UX |
| 3,697,419 | 10/1972 | Grant | 260/112 R X |
| 3,738,933 | 6/1973 | Hollo et al. | 260/112 R X |
| 3,835,041 | 9/1974 | Grant | 260/112 R X |
| 3,838,143 | 9/1974 | Grant | 260/112 R |
| 3,862,901 | 1/1975 | Wennerblom et al. | 260/112 R X |
| 3,899,419 | 8/1975 | Emanuel | 260/112 R X |
| 3,936,375 | 2/1976 | Nettli | 260/112 R X |
| 3,974,069 | 8/1976 | Nettli | 260/112 R |
| 4,119,495 | 10/1978 | Belyaev et al. | 260/112 R X |
| 4,256,630 | 3/1981 | Fremont | 260/112 R |

OTHER PUBLICATIONS

Lab Manual of Analytical Methods of Protein Chemistry, vol. I, pp. 69–76, Alexander et al. (1960).
The Proteins, vol. III, (1965), Neurath, pp. 13–27 & 80–82.
Principals of Chem. Engineering, Walker et al. (1937), pp. 427 & 439–440.
McGraw Hill Encyclopedia of Science and Technology, pp. 78–82.
Exhibit A: Public disclosure by applicant more than 1 year prior to 3/31/76.
Exhibit B: Research Proposal (Carberry et al.) submitted more than 1 year prior to 3/31/76.
Duolite Data Leaflet No. 4, May, 1972.

*Primary Examiner*—Howard E. Schain
*Attorney, Agent, or Firm*—Alexis Barron

[57] ABSTRACT

Nutritious materials, including proteins, are separated from acidic waste-activated sludge in a process which comprises:
(A) converting by physical means active bacteria in said sludge to an inactive form;
(B) subjecting the acidic sludge to an adsorbent material which is capable of adsorbing said proteinaceous material in an uncharged state from said sludge;
(C) extracting said proteinaceous material from said adsorbent material by contacting it with an alkaline material having a cationic species to form a mixture of said separated proteinaceous material and said alkaline material; and
(D) separating said proteinaceous material from said cationic species and other cations by contacting said mixture with a cation exchange resin.

20 Claims, 3 Drawing Figures

EXTRACTION OF NUTRITIOUS MATERIALS FROM ACIDIC SLUDGE WASTE SOLIDS BY ADSORPTION

CROSS-REFERENCE TO RELATED APPLICATIONS

This is a continuation of application Ser. No. 540,993 filed on Oct. 11, 1983 now abandoned, which is a continuation of application Ser. No. 165,084, filed July 1, 1980, now abandoned, which was a continuation-in-part of application Ser. No. 887,871, filed Mar. 20, 1978, now abandoned, which was a continuation of application Ser. No. 672,349, filed Mar. 31, 1976, now abandoned.

FIELD OF THE INVENTION

This invention relates to the extraction of nutritious materials from waste solids, such as for example, waste activated sludge produced by sewage treatment plants.

Rapid population and industrial growth paralleled by more stringent water pollution control requirements have caused the increased dependence on biological secondary treatment to a greater degree than ever before. Concomitant with this higher degree of treatment is the increased production of waste solids realized by the treatment process. Indeed, the flow of waste biological solids projected for the year 1970 was 120 million gallons per day or approximately 3.65 million tons of dried solids per year.

In the past, waste activated sludge has been considered a solid waste management problem. As such, traditional sludge treatment and disposal practices relied heavily on a throw-away technology. Already, disposal of these solids accounts for a sizeable portion of the waste treatment dollar, for example, 24–50% of total treatment expenditures relative to plant size, or at least $50–60 per dry ton. Clearly, as disposal costs rise and the availability of sound disposal sites diminishes, and as the supplies of food and raw materials predictably decline, the prevailing world economic situation might well dictate that waste activated sludge become a valuable resource rather than a waste product.

It has been proposed recently that waste activated sludge be considered a resource for the extraction of useful products and by-products, for example, plastics, composts, and protein. As to proteins, they have been recovered from primary sewage sludge with a solvent extraction scheme utilizing ethylene dichloride and isopropyl alcohol. Similarly, proteins have been extracted from wastewater treatment effluents with an ion-exchange system.

However, a considerably greater quantity of protein is present in the activated sludge micro-organisms which remove biodegradable organics from wastewater, utilizing these organics as a substance from which energy is obtained and more microbes are produced. After separation from the wastewater flow, a portion of these micro-organisms is recycled for reuse within the plant, but the remaining fraction, termed "waste activated sludge", must be disposed.

Sludges, specifically activated sludge, have been analyzed for amino acids with widely varying results. Of the twenty known amino acids, Hurwitz has found fourteen, not including asparaginine, glutamine, alanine, proline, serine, and glutamic acid. On the other hand, activated sludge in India has been shown to contain seventeen amino acids, tryptophan, asparaginine, and glutamine not having been present. Accordingly, generalizations concerning the amino acid content of activated sludge should not be encouraged since it is dependent on the cell population which varies with different wastewaters. However, Tannenbaum has reported that few single cell protein sources contain adequate concentrations of sulfur-containing amino acids.

The suitability of activated sludge as an amino acid source has been most convincingly demonstrated by Tannenbaum, Mateles, and Capco. And it is accepted now that activated sludge is a protein or amino acid source of reasonable quality.

Reported Developments

The separation and purification of proteins have been previously documented in great detail. As is the case with other chemical species, proteins respond to environmental changes in a manner that will minimize the free energy of the system in which they exist. In this light, a search for a technique of protein isolation is reduced to a search for an energy minimum in which the protein portion of the system is most stable. Protein separation procedures fall into three general categories: (1) separation by solubility differences; (2) precipitation as salts; (3) separation by acid-base behavior.

Extractions by solubility differences are influenced by four important parameters: (1) pH, (2) ionic strength, (3) temperature, and (4) dielectric properties of the solvent. Nearly all globular proteins are of minimal solubility at their isoelectric pH because at this pH the protein molecule has no net positive or negative charge. This condition causes electrostatic repulsion to be minimized, allowing individual protein molecules to coalesce into protein aggregates and ultimately precipitate from solution. This technique is known as isoelectric precipitation. As to ionic strength, neutral salts have pronounced dual effects on protein solutions. In low concentrations, the addition of $MgCl_2$ or $MgSO_4$ will increase the solubility of many proteins. This process is termed "salting in" and is caused by the increased dissociation of ionizable groups on the protein chain when in the presence of these salts. However, if the salt concentration is increased, the solubility of the protein decreases and "salting out" occurs. $(NH_4)_2SO_4$ and $Na_2SO_4$ are commonly utilized in this technique although the physical-chemical basis for salting out is not yet clear.

The addition of neutral organic solvents such as acetone and ethanol will decrease the solubility of a protein. These solvents have a dielectric constant lower than water and as such will decrease the hydration of ionic protein groups. Furthermore, the attractive force between two or more protein molecules will be increased, thereby promoting coalescence.

From about 0° to 40° C., proteins will generally increase their solubility with temperature. From 40° to 50° C., however, most proteins become increasingly labile to heat and begin to denature, usually with a loss of solubility at neutral pH.

Most proteins can be completely precipitated from aqueous solutions as salts when certain acids, for example trichloracetic acid or perchloric acid, are added. These reagents form acid insoluble complexes with the protein. Other similar precipitants include tungstic acid, phototungstic acid, and metaphosphoric acid.

The third category of extraction procedures is based on the acid-base behavior of the zwitterionic amino acid molecules of which the proteins are comprised.

It is possible to fractionate proteins on the basis of their characteristic migration rates in an electric field. Proteins migrate much more slowly in an electrical field than do smaller, more simple ions because of their lower charge to mass ratio. There are two basic electrophoretic procedures. (1) In free, or moving boundary electrophoresis, a potential is applied across a pure buffer solution. After a period of time, the proteins are arranged in order of their mobilities and since the refractive index of the prorein-buffer solution is different from the buffer alone, the relative rates of migration can be determined optically for the proteins. (2) In zone electrophoresis, migration across a fixed matrix or gel is measured with qualitative colorimetric methods.

The amphoteric property of polypeptides is exploited when proteins with a net negative or positive charge are attracted and reversibly attached on a synthetic matrix whose charged functional groups displace the protein in solution, that is, ion exchange.

The preceding methods are useful almost exclusively in laboratory applications. Recently, investigators have examined organic solvent extraction, thermal solubilization, and ultracentrifugation as possible industrial scale processes for the recovery of proteins and protein containing bodies in plant and animal matter.

BRIEF DESCRIPTION OF THE INVENTION

In accordance wtih this invention, there is provided a process for extracting nutritious materials, such as proteinaceous materials, from industrially or municipally produced products, for example, process by-products and/or wastes, comprising: (A) subjecting acidic sludge containing proteinaceous material to an adsorbent material which is capable of adsorbing proteinaceous material in an uncharged state, extracting said proteinaceous material from said sludge by adsorbing and maintaining it on said adsorbent material irrespective of any charge possessed by said proteinaceous material; and (B) separating said proteinaceous material from said adsorbent material.

The proteinaceous material can be conveniently separated from the adsorbent material by contacting the same with an alkaline material having a cationic species (for example, an aqueous solution of caustic soda (NaOH)). This results in a mixture of the proteinaceous material and the alkaline material. The proteinaceous material can be separated conveniently from the cationic species of the alkaline material, and, if desired, other metal ions in the mixture by contacting the same with a cationic exchange resin that has an affinity for such cations.

An important aspect of the present invention is pretreatment of waste activated sludge prior to subjecting the sludge to the adsorbent material. Waste activated sludge comprises a two-phase system including finely divided solids in water, said solids, as mentioned above, including micro-organisms which are a source of proteinaceous material. The microorganisms are subjected to a pretreatment step by which physical means are used to convert active bacteria present to an inactive form. This can be done, for example, by conventional high pressure crushing techniques which rupture or lyse the bacterial cells, and makes available nutritious material which can be adsorbed according to the present invention.

The process of the present invention can be used to recover proteinaceous materials from various types of process by-products and waste materials. The present invention is particularly adaptable to efficient recovery of proteinaceous materials from waste activated sludge produced by municipal sewage treatment plants. The pH of such activated sludge is usually within the range of about 6.5 to about 7.5. In accordance with the present invention, the pH is reduced to about 6 or below. The process of the present invention can be operated at a pH which corresponds to the isoelectric pH of the proteinaceous material of the sludge. Although the isoelectric pH of proteinaceous materials varies depending upon the specific materials involved, the isoelectric pH generally falls within the range of about 3 to about 6. For any specific application, it is recommended that the isoelectric pH of the material being treated be determined and the pH be adjusted accordingly. Work has shown also that, for various applications, the preferred adsorbent material which is referred to in the examples below functions more effectively at a pH below that of the isoelectric pH of the proteinaceous material in the sludge. Accordingly, it is recommended that, for any particular application samples of the sludge be used in connection with an initial determination of the most effective pH to use. In general, it is expected that the pH need not be below about 2. In reducing the initial pH of the activated sludge to the isoelectric pH of the proteinaceous material or other operating pH, appropriate acids, for example, hydrochloric acid, can be used.

It is noted that materials which can be treated in accordance with the present invention can also contain, in addition to the proteinaceous material, carbohydrates and vitamins. In accordance with the present invention, such other materials can also be recovered along with the proteinaceous materials. Such other materials can also be adsorbed by the aforementioned adsorbent material and they can be recovered in a solution which also includes the proteinaceous material.

It should be understood that the use of the adsorbent material to extract proteinaceous material from sludge according to this invention is "true" adsorption which involves a mechanism different from the mechanism involved in ion exchange. There follows hereafter a discussion of adsorption and ion exchange and the basic differences which distinguish one from the other.

Adsorption involves complex surface interactions between solute molecules (for example, protein molecules) and adjacent surfaces (the solid adsorbent material). It is generally accepted that in adsorption, the solute molecules are attracted to the solid surface of the adsorbent material due to: (1) Van der Waals forces; (2) electrostatic interactions of weak polarized functional groups on the solute molecule and unsatisfied lattice charges on the surface of the solid adsorbent material; or (3) the formation of weak chemical bonds. The binding energy required for the third case is greater than that for the first two cases, and once this type of "chemisorption" occurs, it is more difficult to recover the adsorbed material.

In contrast, ion exchange occurs only between ionized species. Normally, the ionized functional groups of a solute in bulk solution exchange positions with a finite number of ionizable active sites on a resin particle surface. Two types of resin active sites are manufactured. Strong acid and strong basic sites are ionized at all pH's, and a constant amount of exchange occurs throughout the pH range. On the other hand, weak acid and weak base resins are ionized only at near neutral pH's, and little exchange between the resin and bulk solution occurs at either low or high pH's.

In ion exchange, the mobile ion of an ionizable functional group of the solute molecule must exchange position with an ion of like charge which is associated with the exchange resin. A one-for-one exchange, that is, mass transfer of charged species occurs and chemical bonding is involved. Regeneration of the ion exchange material involves a similar mass transfer between the ion exchange material and a liquid regenerating material.

In contrast, adsorption does not involve the aforementioned type of mass transfer in that there is no transfer of mass from the adsorbent material to the material contacted. Similarly, when recovering the adsorbed material from the adsorbent material, there is no transfer of mass to the adsorbent material. And whereas ion exchange depends on the presence of exchangeable ionized species in both of the media, this is not true of adsorption.

Adsorbents which are capable of adsorbing nutritious materials from sludge in accordance with this invention are known materials and are available commercially. While materials which so function are known, it is believed that they have never been used or proposed for use in the type of application to which this invention relates. Speaking generally, adsorbents for use in the practice of this invention can comprise resinous materials, examples of which include cross-linked phenol formaldehyde condensate resins. It should be understood that other resinous materials which are capable of selectively adsorbing proteinaceous materials from a mixture of constituents in acidic medium can be used.

Compared to the present invention, other protein extraction procedures have the following disadvantages or shortcomings. For example, electrophoresis and temperature methods are used effectively on a laboratory scale basis only. Precipitation processes have the shortcoming that both proteins and waste cell fragments are affected, and thus, such processes are not immune to solids interference.

DETAILED DESCRIPTION OF THE INVENTION

Cell lysis of the activated sludge micro-organisms, accomplished, for example, with a Gaulin Corporation Two Stage Laboratory Homogenizer 15M-8TA, is the first step in the procedure. Sludge homogenate is then passed through the primary fixed bed of an adsorbent resin, for example, Duolite S-761 which is specifically sensitive to proteins. The proteinaceous substance adsorbed on the adsorbent resin is eluted with 2% caustic soda solution and passed through the secondary fixed bed composed of a cation exchange resin, for example Duolite C-25D, which extracts heavy metals and some non-ionic organics (See FIG. 1).

Use of the Gaulin Two Stage Homogenizer for cell lysis is known. Basically, the apparatus is a positive displacement pump which operates at a constant flow of 15 gal/hr (57 l/hr) under all pressures. Flow is pumped through a 0.02 inch orifice into a variable volume cylinder housing. Homogenizing pressure may be varied by a movable cylindrical homogenization valve which varies the volume of the cylinder housing, depending on its position relative to the orifice. Pressures in this stage can be held at 8,000 psi continuously and 12,000 psi for as long as twenty minutes.

The homogenized slurry undergoes a low pressure polishing homogenization in the second stage. The second stage is similar to the first in construction although 500 psi is the manufacturer's suggested operating pressure.

Because the sludge must flow through a 0.02 inch orifice, incompressible solids of greater diameter must be removed. It was therefore necessary to precondition the activated sludge by screening with a series of U.S. Standard Sieves of 35, 50, 60, and 200 mesh.

Sludge homogenizations were performed in the manner that follows:

(1) Activated sludge was screened with standard sieves down to 200 mesh and the screened sludge placed in the sample hopper.

(2) The homogenizer was activated in an unpressurized mode and the pressure sequentially adjusted to 500 psi in the second stage and 10,000 psi on the first stage.

(3) Homogenization was first carried out in a recycle mode to insure uniformity of pressurization. Then the apparatus was switched to flow through mode.

(4) Above procedure was repeated three times.

The preferred adsorbent resin is Duolite S-761 (Diamond Shamrock Chemical Co., formerly S-30) which is a synthetic granular resin designed to adsorb organic impurities from food and drug processing streams. Duolite S-761 has been used successfully to extract Vitamin B-12, penicillin, lactose, and proteins from sugar solutions on a commercial basis.

Flow rates are governed by diffusion. Slower rates are used for high viscosity solutions or for materials of high molecular weight. For most applications the optimal flow rate falls in the range of 0.5 to 1.5 gallons per minute per cubic foot (gpm/ft$^3$) or 4 to 12 bed volumes per hour (bv/hr).

Regeneration and elution are most frequently carried out by treatment with dilute caustic soda followed by neutralization with mineral acid. The suggested dosage of alkali is 2 lbs/ft$^3$ applied in a 2% aqueous solution at 0.5 gpm/ft$^3$ (4 bv/hr). Excess regenerant is washed from the resin when elution is complete; completion of elution is indicated by a change in color from the active orange condition to the black salt form. The resin is then neutralized with 0.5 lbs/ft$^3$ HCl in 0.5-1.0% solution at 1.0 gpm/ft$^3$ (8 bv/hr). In this step, it is necessary to add only that amount of acid to prevent alkaline leaching. Finally, the resin is rinsed with water until the bed pH=4. For this work, homogenate pH was adjusted with concentrated HCl to pH=5, the approximate isoelectric point of most proteins.

Elution and regeneration of the adsorbent resin, as described, is different from typical ion exchange processes in which the ion exchange resin is eluted and regenerated in a one-step treatment which replaces the ions lost and displaces the ions gained.

In operation, 150 cm$^3$ of fresh Duolite S-761 was placed in a clean plexiglas column with an inner diameter of 1.5 inches (3.8 cm) producing a fixed bed 5 inches (13 cm) in height. The bed rested on a woven polyester pad and a 35 mesh screen to prevent resin loss. Service flow for the primary bed was 0.2 gpm/ft$^3$ (1.5 bv/hr; 4-5 ml/min). The bed was eluted with 640 mls of 2% caustic soda at 0.2 gpm/ft³ thereby yielding a proteinaceous material at high pH.

Build-up of solids at the adsorbent resin-liquid interface was encountered. Even though the activated sludge had been homogenized under extreme pressure stress, a measurable amount of residual solids remained that served to clog resin interstices. Further, fouling was increasing due to isoelectric precipitation at the resin-liquid interface.

In order to minimize the effect of interfacial solids build-up, a solubilizing agent was added to the homogenate prior to treatment on the primary bed. The solubilizing agent used for this research was sodium lauryl sulfate ($NaC_{12}H_{25}SO_4$), a surfactant. Surfactants and wetting agents suspend particles in solution, especially organic particles. For this use, the detergent should be nitrogen free and effective at low dosages.

For removing cations from the elute extracted from the adsorbent material, a highly porous strong-acid cation exchange resin, preferably Duolite C-25D (Diamond Shamrock Co.), is used. C-25D is characterized by rapid exchange rate, low rinse requirement, and maximum removal of monovalent cations. It is especially useful in de-ionizing waters which contain a high ratio of sodium to total cations. The suggested service flow is 1–5 gpm/ft³ (8–40 bv/hr). Regeneration may be accomplished with 6–12% HCl or 2–8T $H_2SO_4$ applied at 0.5–1.5 gpm/ft³ (4–12 bv/hr).

In this work, C-25D beds of 225 mls were placed in the plexiglas column described previously. A measured volume of primary bed eluent was applied to the C-25D secondary bed at 2 gpm./ft³ (16 bv/hr; 60 ml/min).

Figure 1:
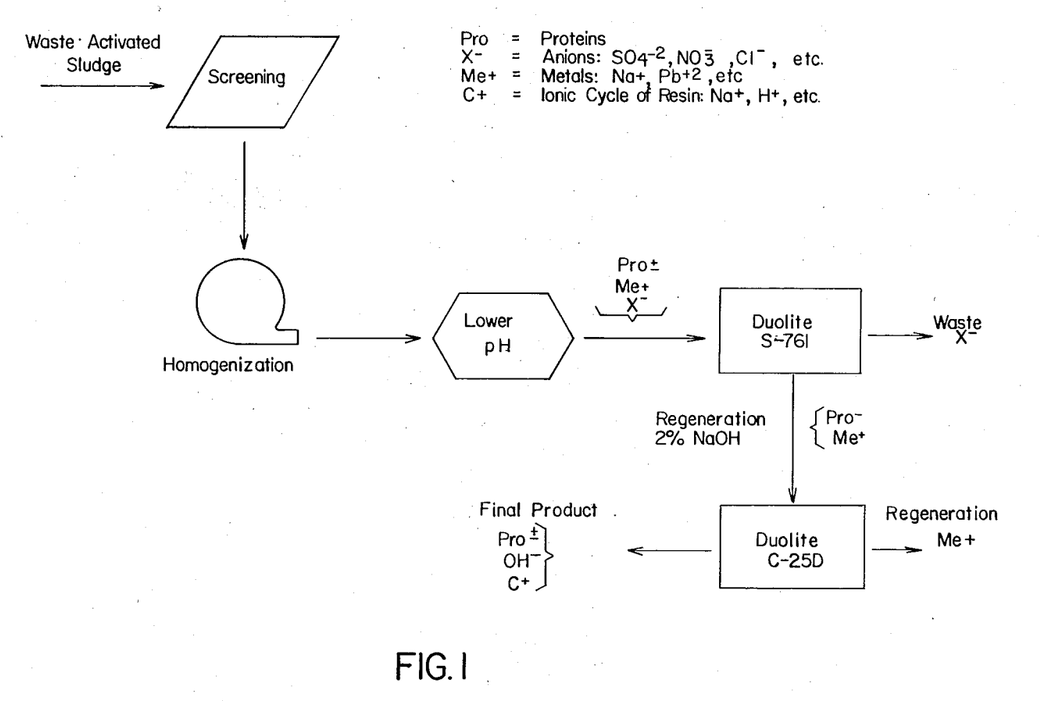
FIG. 1 is a process flow chart showing process steps used in the practice of the present invention.

A flow chart describing an embodiment of the extraction process is presented in FIG. 1. First, waste activated sludge was screened down to 200 mesh to remove incompressibles which might harm the homogenizer orifice. Then the screened sludge was homogenized three times at 10,000 psi. The activated sludge, once homogenized, results in an admixture of proteins and undesirable materials. The latter interfering substances include anions, such as $Cl^-$, $SO_4^{-2}$, and $NO_3^-$, dissolved ammonia, and metallic cations, such as $Pb^{+2}$, $Hg^{+2}$, $Cd^{+2}$, $Cu^{+2}$, and $Cr^{+2}$.

After cell lysis, the suspension which existed at approximately neutral pH was acidified with concentrated hydrochloric acid to pH=5.0. At this point, the solution contained proteins in their uncharged state ($Pro^\pm$), metal ions ($Me^+$), radical anions ($X^-$), and fragmentary cell debris. This pH value was selected because the resin of the primary bed had been reported to have optimal recovery of proteins at or near their isoelectric point, $5.0 < pH < 5.5$. At this pH, a large portion of the metallic ions was chelated with the proteins.

After lysis and acidification, the homogenate flowed through a fixed bed of Duolite S-761 adsorbent. Here, the protein-metallo complex was removed while anions and uncomplexed cations were allowed to pass through. The complexed proteins and metals were then recovered by eluting the resin with 2% caustic soda. The pH of the eluent was generally 13.2–13.8, sufficiently high to destroy the metal complex, and precipitate the more insoluble metals in their hydroxide form.

The more soluble heavy metals and proteins in solution were then treated in a bed of Duolite C-25D cation exchange resin. This bed displaced the remaining metal ions with sodium ions, realizing a product which consisted of proteins, sodium, and hydroxide ions at high pH. If the C-25D bed were on a hydrogen cycle, the metal ions would be displaced by hydrogen ions and a product of protein, $H^+$ and $OH^-$ or protein and water would have resulted. The secondary bed was not operated on a hydrogen cycle in this work, however, since the proteins would become excessively protonated. Under such conditions, the positively charged proteins would be removed by the C-25D along with the metals. This phenomenon will be discussed below.

EXAMPLES

Two examples are described hereafter. The two examples are identical, with the exception of the use of 0.1% by weight sodium lauryl sulfate, as a solubilizing agent, in the example referred to as the "digested run" while the other example, without sodium lauryl sulfate is termed "undigested run".

The sludge, with a suspended solids concentration of 0.8364%, was homogenized readily with negligible settling of solids until the pH was adjusted to 5. At this point, a dramatic change occurred in which a previously homogeneous suspension of micro-fines autoflocculated, and solids separated into a two-phase system. Previously homogenates had been observed to be stable for as long as several weeks following homogenization. Since a pH of 5 approximates the isoelectric point of most proteins, flocculation enhanced by isoelectric precipitation was the suspected cause of this effect. Assuredly, solids separation is undesirable, for then the bed behaves similarly to a gravity sand filter and solids build up on the bed surface and cannot be adsorbed within the bed. The data for this undigested run is shown in Table 1 below.

TABLE 1

| | Undigested Run | | | | | | |
|---|---|---|---|---|---|---|---|
| | Total N mg | $NO_3$—N mg | $NH_3$—N mg | | Pb mg/l | Cd mg/l | $F_e$ mg/l |
| Homogenate | 178.20 | 0.40 | 37.23 | 5.13 | ~0 | 0.0080 | 0.5 |
| Primary (S-761) Eluent | 90.89 | ~0 | 7.79 | 13.30 | 0.65 | 0.0160 | 0.9 |
| Waste Fraction | 63.19 | 0.43 | 29.02 | 5.00 | — | — | — |
| Final Product | 65.26 | 0.07 | 8.83 | 13.30 | 0.55 | 0.0150 | 0.5 |

S-761 Bed Volume = 150 cm³
S-761 Service Flow = 5 mls/min
S-761 Regeneration Flow = 4 mls/min
S-761 Bed pH = 4.00
C-25 D Bed Volume = cm³
C-25 D Service Flow = 60 mls/min
Sludge Solids Concentration = 1.016%
Sludge % N = 4.9

Although organic nitrogen was used to determine protein content, total nitrogen was used originally as a first approximation, since the measured inorganic nitrogen concentrations were found to be insignificant. Total nitrogen was measured at four key points in the system. These were (1) the dried sludge solids, (2) the homogenate, (3) the eluent from the primary bed, S-761, and (4) the final product after treatment on the secondary bed, C-25 D.

The dried sludge solids were found to have an average of 8.265% nitrogen or 51.656% protein. The total nitrogen in the 500 ml sample was 254.42 mg or 73.61% of the total amount of nitrogen available from the sludge. The loss of 26.39% of the total available nitrogen can be attributed to the manner of storage of the homogenate.

The homogenate was stored at 5° C. for 48 hours to test the stability of the suspension. During this time, some of the solids did settle out although a vast majority remained in suspension. These solids were not included in the homogenate used for extraction because it was reasoned that they would only serve to foul the column.

In order to harvest the proteinaceous material captured in the primary bed, it was eluted with 540 mls of 2% caustic soda solution, twice the manufacturer's suggested volume. A 26.76% recovery of nitrogen from the homogenate was realized from the primary bed elution with an additional 11.36% found in the waste fraction. "Waste fraction" refers to effluent from the primary bed and is composed of materials not adsorbed by the column.

Figure 2:
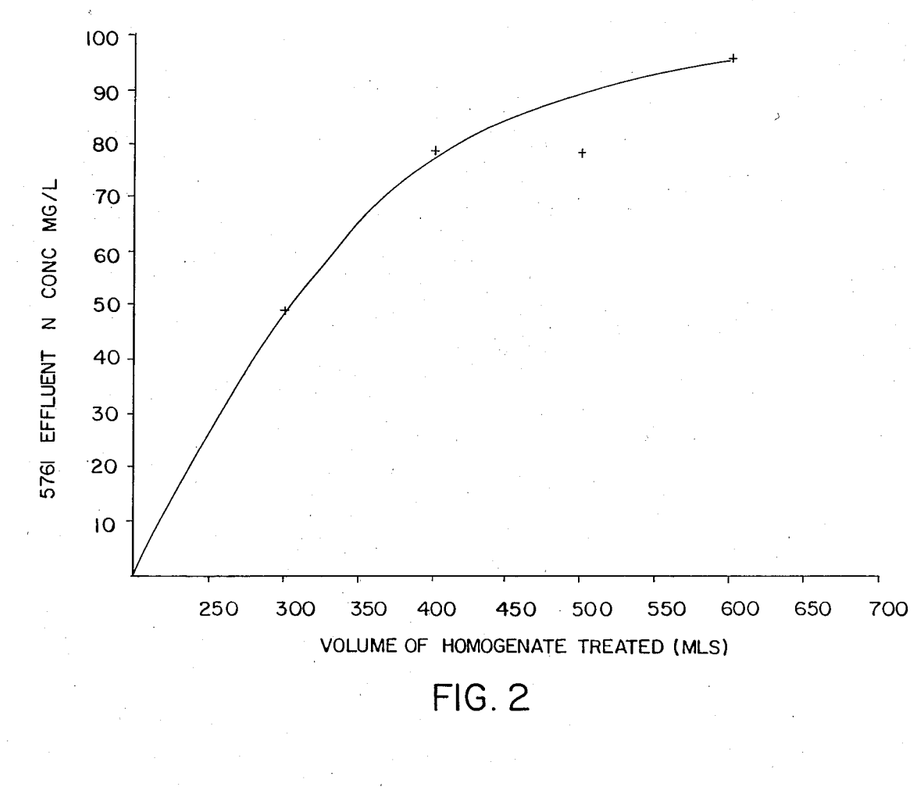
FIG. 2 is a graph showing results obtained from experimental work described hereinbelow.

11.36% of the nitrogen was not captured in the column due to geometric considerations of the apparatus. Nitrogen levels in the sludge approached analytical detection limits. Therefore, nitrogen concentrations could not be diluted by large elution volumes. Since twice the prescribed volume of caustic was needed to elute the bed, the ratio of eluent volume to bed volume was 4:1. It was necessary to limit the bed to an optimum bed volume/sample size. For the homogenate sample size readily prepared from waste activated sludge, 500 mls, 150 mls was determined to be an optimum bed volume. However, if the 150 ml bed had been in the prescribed geometry, the column dimensions would need to be 36 inches high by 0.57 inches in diameter (91.44 cm by 1.45 cm). Such dimensions were believed to be unrealistic on a laboratory scale. Break through studies (see FIG. 2) showed that the column never reached complete exhaustion through the entire run. The nitrogen content of the waste fraction, therefore, was due to geometrical effects. Removal in a bed of proper dimensions should approach 38.12%.

The remaining 61.88% nitrogen was trapped in the solids that fouled the upper portion of the bed, and were not adsorbed and subsequently eluted from the resin. This loss may be minimized by altering the bed configuration.

The secondary bed of C-25D showed a 41.68% recovery from the primary eluent. The efficiency of the bed can be more understandable when characteristics of the C-25D resin are considered. C-25D removed metallic ions and uncharged organics from solution at any pH>1. This resin is most useful for deionizing waters having a high Na+ to total cation ration. This latter property made C-25D attractive for this work for removing the 2% NaOH used in eluting the primary bed. Although all the ionizable amino acid groups were charged in the influent of the secondary bed (pH=13.0-13.8), uncharged nitrogen compounds were removed by the column. The low recovery due to this loss in the secondary bed may be improved by use of a different resin or by changing operating parameters so as to minimize nitrogen removal.

Under operating conditions utilized in this run, overall recovery of the total process was 11.15%.

It is known to use total nitrogen as an indication of protein content. However, it has been reported that organic nitrogen is a better protein measure in wastewater. Accordingly, nitrate and ammonia measurements were made at the same points of total nitrogen measurement and used to calculate organic nitrogen. Table 1 indicates that Elkton sludge possessed a low $NO_3^-$ to $NH_3$ ratio (0.16 to 39.57 mg a, N), and these concentrations totaling 19.17 mg accounted for 7.75% of the total nitrogen.

Separation of inorganic nitrogen from protein in the primary bed was considerable. The stream which exited the bed contained 68.75% of the nitrate and 75.10% of the ammonia that entered the bed. Failure to achieve a nitrate mass balance was due to the level of precision of the ion probe ($\pm 0.1$ ppm-$NO_3$) at the low nitrate concentration present. Ammonia is present in the primary eluent because of the affinity proteins have for dissolved ammonia. Steinhardt and Beychok have documented the formation constant for protein complexation as seen in Table 2 below. The protein-ammonia complexation constant indicates that ammonia is transported with the protein and volatilized at high pH.

TABLE 2

| | Over-all Constants Log ($K_n$) of Complexes of Amino Acids (and One Dipeptide) with Metals | | | | | | | | | |
|---|---|---|---|---|---|---|---|---|---|---|
| Amino Acid | $pK^3NH_{3+}$ | $Cu^{2+}$ | $Ni^{2+}$ | $Zn^{2+}$ | $Co^{2+}$ | $Cd^{2+}$ | $Fe^{2+}$ | $Mn^{2+}$ | $Mg^{2+}$ | $Fe^{3+}$ |
| Glycine | 9.86 | 15.4 | 11.0 | 9.3 | 8.9 | 8.1 | 7.8 | 5.5 | 4 | 0 |
| L-Proline | 10.68 | 16.8 | 11.3 | 10.2 | 9.3 | 8.7 | 8.3 | 5.5 | 4 | 0 |
| DL-Tryptophan | 9.55 | 15.9 | 10.2 | 9.3 | 8.5 | 8.1 | 7.6 | 5.0 | 4 | 0 |
| L-Asparagine | 8.55 | 14.9 | 10.6 | 8.7 | 8.4 | 6.8 | 6.5 | 4.5 | 4 | 0 |
| DL-Alantine | 9.97 | 15.1 | — | — | 8.4 | 7.3 | — | — | — | — |
| DL-Valine | 9.72 | 15.1 | — | — | 8.6 | — | 6.8 | — | — | — |
| DL-Phenylalanine | 9.31 | 14.9 | — | — | 7.9 | — | 6.3 | — | — | — |
| DL-Serine | 9.24 | 14.6 | — | — | 8.0 | — | 7.0 | — | — | — |
| DL-Methionine | 9.34 | 14.7 | — | — | 7.9 | — | 6.7 | — | — | — |
| β-Alanine | 10.36 | 12.9 | — | — | 7.0 | — | 4.0 | — | — | — |
| L-Tyrosine | — | 15.0 | 10.1 | 9.1 | 8.1 | — | 7.1 | 2.4 | 2 | — |
| L-Lysine | — | 13.7 | 8.8 | 7.5 | 6.8 | — | 7.1 | 2.0 | — | — |
| L-Glutamic Acid | — | — | 10.3 | 8.5 | 8.1 | — | 4.6 | 3.0 | — | — |
| Glycylglycine | — | 11.7 | 7.9 | 6.6 | 5.9 | — | — | 2.2 | 1.1 | — |

12 mg or 30.33% of the total ammonia was not accounted for in the primary eluent due to volatilization. The eluent pH was sufficiently high to convert ammonium ion to ammonia:

Dissolved ammonia gas is extremely volatile and was easily lost to the atmosphere under prevailing experimental conditions.

Protein mass was determined by multiplication of the organic nitrogen by 6.25. Based on organic nitrogen concentration, protein recovery efficiency figures were 26.57% for the primary bed, 50.53% for the secondary bed, and 10.12% for the overall process.

Table 3 below shows the types and concentrations of heavy metals in activated sludge found by Hurwitz.

TABLE 3

Metal Content of Activated Sludge

| COMMON IONS | | TRACE METALS (SPECTROMETRIC ANALYSIS) | |
|---|---|---|---|
| PERCENT (DRY BASIS) | | | |
| ALUMINUM | 3–4 percent | BORON | 0.002 percent |
| CALCIUM | 2–3 percent | CHROMIUM | 0.1 percent |
| IRON | 5–6 percent | COPPER | 0.1 percent |
| MAGNESIUM | 0.5–1 percent | LEAD | 0.1 percent |
| SILICON | 5–6 percent | MANGANESE | 0.1 percent |
| SULFATE ($SO_4$) | 1 percent | NICKEL | 0.1 percent |
| PHOSPHATE ($P_2O_5$) | 5–6 percent | POTASSIUM | 0.1 percent |
| | | SILVER | 0.1 percent |
| | | TIN | 0.1 percent |
| | | TITANIUM | 0.1 percent |
| | | ZINC | 0.1 percent |
| | | COBALT | 8–16 ppm |

Iron, lead, and cadmium were chosen as indicators for metal removal efficiency in this work. These ions possess high solibility and low charge to mass ratio rendering them more difficult to remove by precipitation and ion exchange. Furthermore, Hurwitz's data indicated that these ions would be present in measurable concentrations. Table 1 illustrates the fate of heavy metals in this work.

The concentrations of iron and cadmium in the homogenized activated sludge were 0.5 and 0.0065 ppm respectively, while no detectible lead was found. No separation of metallic cations from proteins was expected in the first column since these ions were strongly complexed (See Table 2).

Possible heavy metal removal mechanisms were precipitation and ion exchange. Elution of the primary bed at high pH destroyed the complex and the metals could be precipitated as hydroxides. Removal via precipitation was nonexistent, however, as evidenced by comparison of metal concentrations in the homogenate and the primary bed eluent. The alternative ion exchange mechanism must be considered as a removal mechanism by comparing metal concentrations in the primary bed eluent to those in the final product. Only cadmium exhibited marginal removal in the secondary column. The failure to achieve better metal removal might have been due to the initially low metal concentration of the sludge. Since no hydroxide precipitate was formed at pH=13.89, metal concentrations might have been so low initially that these ions would remain soluble at any pH. In addition, a sufficiently large concentration gradient to cause removal may not have existed between the resin and liquid phase of the secondary bed. Compared to values in Table 3, the metal content of Elkton activated sludge was substantially lower than Hurwitz's values. The influent to the Elkton plant is 100% domestic in origin and would be characterized by low anticipated metal concentrations; Hurwitz's figures reflected values for sludges of large municipalities with a sizable industrial contribution to the influent.

The final metal ion concentrations of 0.0, 0.0060, and 0.5 ppm for lead, cadmium, and iron, respectively, were difficult to evaluate as contaminant concentrations as a potential livestock feed. The United States Food and Drug Administration stipulated no guidelines for the heavy metal content of animal feed.

On the other hand, comparison of the liquid product with drinking water standards is encouraging. The 1962 Revised Public Health Service Drinking Water Standards limited cadmium, lead, and iron to 0.01, 0.05, and 0.3 ppm, respectively. The data in Table 1 show that cadmium and lead were within allowable limits. Iron, though, is 0.2 ppm over the standard. But the drinking water standards also state that, "The amount of iron permitted in water by qualify control is to prevent objectionable taste and laundry staining and constitutes only a small fraction of the amount normally consumed and is not likely to have any toxicological significance." The standards also reported that iron is found in diets to levels as high as 35 mg/day (53). Due to the lack of iron toxicity, it can be said that the final product of the undigested process is sufficiently low in those heavy metals tested so as to be in accordance with drinking water standards.

The procedure and sampling methods for the digested run were identical to those for the undigested run with one excaption. Because of solids interference experienced in the undigested run, 0.1% sodium lauryl sulfate was added to sludge with an original suspended solids content of 1.016%. Besides differing in solids content, the sludge also contained 42.16% less nitrogen than the sludge used for the digested run. A summary of the data obtained from the digested run may be found in Table 4 below.

TABLE 4

| | Data from Digested Run | | | | | | |
|---|---|---|---|---|---|---|---|
| | Total N mg | $NO_3$—N mg | $NH_3$—N mg | pH | Pb mg/l | Cd mg/l | $F_e$ mg/l |
| Homogenate | 254.42 | 0.16 | 39.57 | 5.10 | ~0 | 0.0065 | 0.5 |
| Primary (S-761) Eluent | 68.09 | 0.05 | 9.87 | 13.89 | ~0 | 0.0065 | 0.5 |
| Waste Fraction | 28.91 | 0.20 | 17.70 | 4.19 | — | — | — |
| Final Product | 28.38 | 0.55 | 9.62 | 13.20 | ~0 | 0.0060 | 0.5 |

S-761 Bed Volume = 150 cm$^3$
S-761 Service Flow = 4 mls/min
S-761 Regenerant Flow = 4 mls/min
S-761 Bed pH = 4.30
C-25 D Bed Volume = 230 cm$^3$
C-25 D Service Flow = 60 mls/min
Sludge Solids Concentration = 0.8364%
Sludge % N = 8.3

Figure 3:
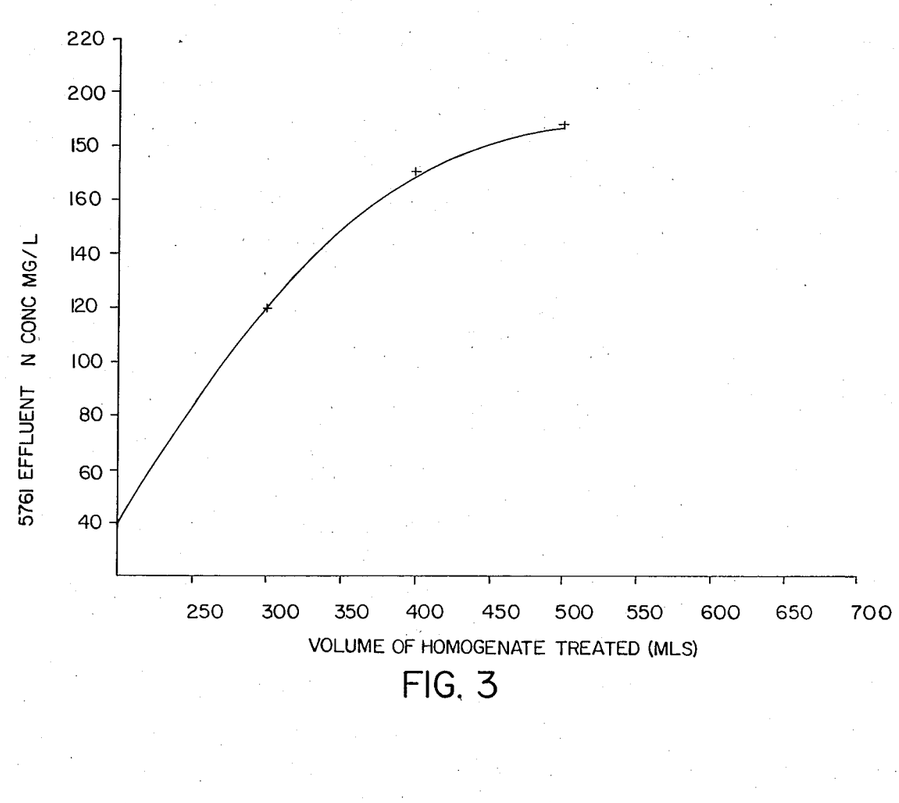
FIG. 3 is a graph showing results obtained from experimental work described below.

Of the 178.20 mg of total nitrogen in the homogenate, 90.89 mg was recovered by elution of the primary column for an efficiency of 51.00%. However, breakthrough studies shown in FIG. 3 show that the column leaked nitrogen much earlier than did the undigested system. An accelerated exhaustion of the bed was caused by the presence of the sodium lauryl sulfate, to which the Duolite S-761 was sensitive. By altering bed configuration and operational parameters, the nitrogen in the waste fraction would become recoverable, thereby increasing the efficiency to 86.46%.

In the secondary bed, a 20.09% loss of nitrogen was experienced probably due to removal of uncharged, non-proteinaceous, nitrogen-containing organics. Although this phenomenon lowers the overall efficiency to 40.75%, optimization of a pilot plant scale operation should eliminate losses on both beds, increasing the efficiency to 90% or more.

As in the undigested process, inorganic nitrogen removal in the digested run was significant. 100% nitrate removal was obtained in the first bed while 79.08% of the ammonia was separated by the S-761. The total inorganic nitrogen removal was 90.45%. The apparent lack of an ammonia balance is due once again to volatilization of ammonia gas. The increase of 0.07 ppm nitrate in the second column was due to either analytical limitations or breakdown of the Langmuir approximation at extreme ionic strength.

Comparison of Table 4 with Table 1 shows that the metal content of the sludges in the digested and undigested run were virtually identical. The metal removals for the digested system were drastically different, however. The apparent increase in metals concentration during treatment on the primary bed has two possible explanations. First, the apparent increase of metals concentration fell within the realm of experimental error for iron and cadmium analyses. The measured increase in lead concentration, however, cannot be entirely explained by experimental error. Increases in lead concentration not accounted for by experimental error must be due to concentration on the bed. Volumes of homogenate, primary bed eluent, and secondary bed product were 689, 473, and 425 mls, respectively. These volume changes were enough to increase the metals concentration after treatment on the first bed. Calculations performed show that the apparent anomalous behavior of lead in the digested system might best be explained by a combination of analytical error and volume effects.

The preferred adsorbent material for use in the practice of the invention has been described. This material is a cross-linked phenol formaldehyde condensate resin which functions as an ion exchange material in alkaline medium, for example, at a pH above about 9.5, and as an adsorbent in acidic medium.

Other resins capable of being used in the practice of the present invention are described in U.S. Pat. No. 2,389,865. It should be understood that the resins described in this patent are exemplary, and that other adsorbent materials can be used also.

In summary, both digested and undigested systems were evaluated. Due to solids interference in the undigested run and relative efficiencies, the digested process was preferred. Under optimal industrial scale conditions, a nitrogen and therefore protein, recovery greater than 90% should be expected with a greater than 90% removal of inorganic nitrogen. Furthermore, the product had a heavy metal content that conforms to the United States Public Health Drinking Water Standards.

Activated sludge, traditionally considered a waste disposal problem, was shown to be a nutritional resource of considerable quality and quantity. To capitalize upon the food value of waste activated sludge, a dual bed adsorbent-cation exchange system was studied to determine its efficiency for protein recovery. Data from two final runs were compared, and the system incorporating sodium lauryl sulfate to retard solids interference was preferred.

The product of the system was assayed and reported to be high in protein content while low in inorganic nitrogen, radical anions and heavy metals tested. The efficiency of the unoptimized laboratory scale apparatus was found to be 56.91%. Recoveries greater than 90% would be expected in an optimized continuous counter-current flow configuration in which bed fouling due to solids interference would be eliminated.

I claim:

1. A process for extracting nutritious material from waste sludge having a water phase and comprising finely divided solids in said water phase, said solids including microorganisms which are a source of proteinaceous material, said process comprising treating said microorganism to effect the release of said proteinaceous material into the water phase of said sludge, subjecting said sludge containing said proteinaceous material in said water phase to a resinous adsorbent material in an uncharged state, extracting said proteinaceous material from said water phase by adsorbing and maintaining it on said adsorbant material irrespective of any charge possessed by the proteinaceous material, said adsorption being effected in the absence of transfer of mass from said absorbent material to said water phase, and separating said proteinaceous material from said absorbent material, said separation being effected in the absence of transfer of mass from said water phase to said absorbent material, and wherein the sludge which is subjected to said absorbent material is acidic.

2. A process according to claim 1 wherein said adsorbed proteinaceous material is separated from said adsorbent material by contacting the same with an alkaline material having a cationic species thereby forming a mixture of said separated proteinaceous material and said alkaline material; and including separating said cationic species from said proteinaceous material.

3. A process according to claim 1 wherein said sludge comprises activated sludge including also carbohydrates and vitamines and initially having a pH within the range of about 6.5 to about 7.5 and including adjusting the pH to said isoelectric pH of said proteinaceous material, that is, a pH within the range of about 3 to about 6, and wherein said adsorbent material is a synthetic resinous material which also adsorbs said carbohydrates and vitamins; and separating said proteinaceous material, carbohydrates and vitamins from said resinous material by contacting the same with an aqueous solution of caustic soda (NaOH) thereby producing a mixture of dissolved sodium and said proteinaceous material, carbohydates and vitamins; and separating said dissolved sodium from said mixture by contacting said mixture with a cation exchange resin, thereby producing an aqueous solution of said proteinaceous material, carbohydrates and vitamins substantially free of said dissolved sodium.

4. A process according to claim 3 wherein said solution is also substantially free of heavy metals such as cadmium, lead and iron.

5. A process according to claim 1 wherein said proteinaceous material is caused to be released from said microorganisms by crushing them.

6. A process according to claim 1 wherein said sludge is contacted with said adsorbent material in the presence of a solubilizing agent.

7. A process for extracting nutritious material from waste activated sludge containing proteinaceous material comprising:
(A) homogenizing said sludge;
(B) subjecting said homogenized sludge to an adsorbent material which is capable of adsorbing from said homogenized sludge proteinaceous material in an uncharged state, and extracting said proteinaceous material from said homogenized sludge by adsorbing and maintaining it on said adsorbent material irrespective of any charge possessed by the proteinaceous material, said adsorption being effected in the absence of transfer of mass from said adsorbent material to said sludge; and
(C) separating said proteinaceous material from said adsorbent material, said separation being effected in the absence of transfer of mass from said sludge to said adsorbent material;
wherein the homogenized sludge which is subjected to said adsorbent material is acidic and, if necessary, acidifying said waste activated sludge or said homogenized sludge to render acid the sludge which is subjected to said adsorbent material.

8. A process for extracting nutritious material from waste activated sludge, including bacteria in viable form, and containing proteinaceous material and one or more of the following undesirable materials: chloride; sulfate; nitrate; ammonia; lead; mercury; cadimum; copper; and chromium; said process comprising:
(A) converting by physical means said bacteria in viable form to an inactive form to provide an aqueous solution including proteinaceous material and one or more of said undesirable materials;
(B) subjecting said solution to an adsorbent material which is capable of adsorbing from said solution proteinaceous material in an uncharged state, and extracting proteinaceous material from said solution by adsorbing and maintaining it on said adsorbent material irrespective of any charge possessed by the proteinaceous material, said adsorption being effected in the absence of transfer of mass from said adsorbent material to said sludge;
(C) separating adsorbed proteinaceous material and one or more of said undesirable materials from said adsorbent material to provide a solution containing proteinaceous material and one or more of said undesirable materials, said separation being effected in the absence of transfer of mass from said sludge to said adsorbent material; and
(D) separating proteinaceous material from one or more of said undesirable materials;
wherein the solution which is subjected to said adsorbent material is acidic, and if necessary, acidifying said waste activated sludge or said solution to render acidic the solution which is subjected to said adsorbent material.

9. A process according to claim 7 wherein said sludge is contacted with said adsorbent material in the presence of a solubilizing agent.

10. A process according to claim 1 including using as adsorbent material cross-linked phenol formaldehyde condensate resin.

11. A process according to claim 2 including using as adsorbent material cross-linked phenol formaldehyde condensate resin.

12. A process according to claim 3 including using as adsorbent material cross-linked phenol formaldehyde condensate resin.

13. A process according to claim 4 including using as adsorbent material cross-linked phenol formaldehyde condensate resin.

14. A process according to claim 5 including using as adsorbent material cross-linked phenol formaldehyde condensate resin.

15. A process according to claim 6 including using as adsorbent material cross-linked phenol formaldehyde condensate resin.

16. A process according to claim 7 including using as adsorbent material cross-linked phenol formaldehyde condensate resin.

17. A process according to claim 8 including using as adsorbent material cross-linked phenol formaldehyde condensate resin.

18. A process according to claim 10 wherein the pH of the sludge which is subjected to said adsorbent material is about 3 to about 6.

19. A process according to claim 16 wherein the pH of the sludge which is subjected to said adsorbent material is about 3 to about 6.

20. A process according to claim 17 wherein the pH of the solution which is subjected to said absorbent material is about 3 to about 6.

* * * * *